US010729202B2

(12) United States Patent
Wu

(10) Patent No.: US 10,729,202 B2
(45) Date of Patent: *Aug. 4, 2020

(54) HEADBAND ARRANGEMENT AND WELDING HELMET EQUIPPED WITH THE SAME

(71) Applicant: Tecmen Electronics Co., Ltd., Nanjing (CN)

(72) Inventor: Ziqian Wu, Nanjing (CN)

(73) Assignee: Tecmen Electronics Co., Ltd., Nanjing (CN)

(*) Notice: Subject to any disclaimer, the term of this patent is extended or adjusted under 35 U.S.C. 154(b) by 614 days.

This patent is subject to a terminal disclaimer.

(21) Appl. No.: 15/333,842

(22) Filed: Oct. 25, 2016

(65) Prior Publication Data

US 2018/0042774 A1 Feb. 15, 2018

(30) Foreign Application Priority Data

Aug. 10, 2016 (CN) ...................... 2016 2 0864542 U

(51) Int. Cl.
*A42B 3/14* (2006.01)
*A42B 1/00* (2006.01)
(Continued)

(52) U.S. Cl.
CPC .............. *A42B 3/145* (2013.01); *A42B 1/008* (2013.01); *A42B 3/225* (2013.01); *A42C 5/04* (2013.01); *A61F 9/06* (2013.01)

(58) Field of Classification Search
CPC ........... A42B 3/085; A42B 3/14; A42B 3/324; A42B 3/225; F16P 1/04; F16P 1/06; H01F 7/0242; A61F 9/06
(Continued)

(56) References Cited

U.S. PATENT DOCUMENTS 3,041,622 A * 7/1962 Gurtowski ............. A42B 3/145
2/8.1
5,421,799 A * 6/1995 Rabin .................... A61H 7/006
2/410
(Continued)

OTHER PUBLICATIONS

European Patent Office, Partial European Search Report in European Patent Application No. 17151337 (dated Jul. 11, 2017).
(Continued)

*Primary Examiner* — Khaled Annis

(57) ABSTRACT

The present application relates to a headband arrangement comprising: an attachment structure; and a helmet mounting structure which can be selectively slid along the attachment structure, the helmet mounting structure having a lockable component, the lockable component being pivotable about a pivotal shaft between a locking position and an unlocking position, wherein a first magnetic part is secured in the lockable component, a second magnetic part is secured in the helmet mounting structure or the attachment structure, a repulsive force can be generated between the first and second magnetic parts to drive the lockable component to return from the unlocking position to the locking position and to hold the lockable component in the locking position. The present application also relates to a headband arrangement having a band part for attaching at or adjacent to the back of a user's head, wherein the band part is provided with a sheath for adjusting the band part's length, and a cushion structure is pivotally provided on a side of the sheath facing the back of the user's head. The present application further relates to a welding helmet having one of said headband arrangements.

20 Claims, 5 Drawing Sheets

(51) Int. Cl.
*A42C 5/04* (2006.01)
*A61F 9/06* (2006.01)
*A42B 3/22* (2006.01)

(58) Field of Classification Search
USPC .................................................... 2/415, 418
See application file for complete search history.

(56) References Cited

U.S. PATENT DOCUMENTS

| | | | |
|---|---|---|---|
| 7,000,262 B2 * | 2/2006 | Bielefeld | A42B 3/145 2/418 |
| 7,043,772 B2 * | 5/2006 | Bielefeld | A42B 3/145 2/418 |
| 7,174,575 B1 * | 2/2007 | Scherer | A42B 3/145 2/418 |
| 8,056,150 B2 * | 11/2011 | Stokes | A42B 3/145 2/417 |
| 8,850,624 B2 * | 10/2014 | Gleason | A42B 3/142 2/417 |
| 9,161,588 B2 * | 10/2015 | Chen | A42B 3/145 |
| 2003/0115662 A1 * | 6/2003 | Dobbie | A42B 3/085 2/422 |
| 2004/0172739 A1 * | 9/2004 | Racine | A42B 3/324 2/417 |
| 2005/0138719 A1 * | 6/2005 | Huh | A42B 3/14 2/416 |
| 2006/0070168 A1 * | 4/2006 | Nakabayashi | G02B 27/0176 2/171 |
| 2007/0245467 A1 | 10/2007 | Lilenthal et al. | |
| 2009/0320187 A1 * | 12/2009 | Petzl | A42B 3/14 2/417 |
| 2010/0050325 A1 * | 3/2010 | Wang-Lee | A42B 3/145 2/418 |
| 2010/0095438 A1 * | 4/2010 | Moelker | A42B 3/145 2/418 |
| 2011/0023204 A1 | 2/2011 | Brace | |
| 2011/0088148 A1 * | 4/2011 | Chen | A42B 3/145 2/418 |
| 2011/0191946 A1 * | 8/2011 | Fang | A42B 3/145 2/418 |
| 2012/0066872 A1 | 3/2012 | Eisenberger | |
| 2012/0144567 A1 | 6/2012 | Huh | |
| 2014/0366253 A1 | 12/2014 | Gotti | |
| 2015/0000007 A1 | 1/2015 | Gleason et al. | |
| 2015/0026871 A1 * | 1/2015 | Gotti | A42B 3/0406 2/418 |
| 2015/0047154 A1 | 2/2015 | DeBien | |
| 2015/0059065 A1 * | 3/2015 | Klotz | A42B 3/145 2/418 |
| 2015/0074876 A1 * | 3/2015 | Chiang | A42B 3/145 2/418 |
| 2015/0074877 A1 * | 3/2015 | Huh | A42B 3/225 2/422 |
| 2015/0250251 A1 | 9/2015 | Ahlgren et al. | |
| 2016/0037854 A1 | 2/2016 | Durham et al. | |
| 2016/0051000 A1 * | 2/2016 | Windham | A42B 3/145 2/418 |
| 2017/0238643 A1 * | 8/2017 | Pereira | A42B 3/08 |

OTHER PUBLICATIONS

European Patent Office, Extended European Search Report in European Patent Application No. 17151337 (dated Oct. 16, 2017).
Extended European Search Report regarding Application No. 18210964.5, dated Apr. 10, 2019, 7 pages.
IP Australia, Examination Report No. 1 regarding Application No. 2017200061, dated Jul. 8, 2019, 4 pages.

* cited by examiner

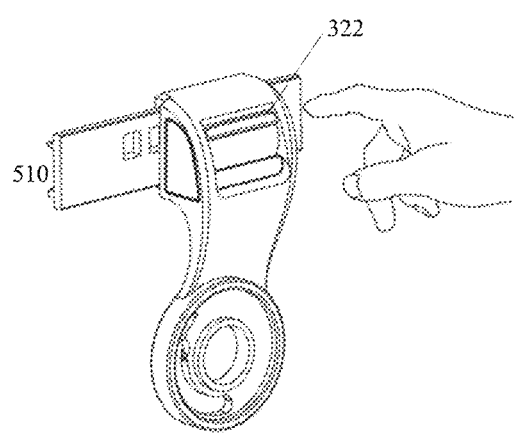 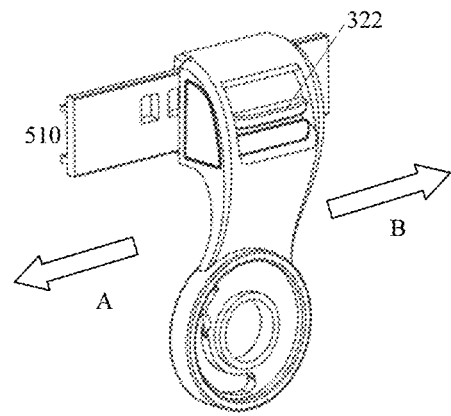
Fig. 4a        Fig. 4b
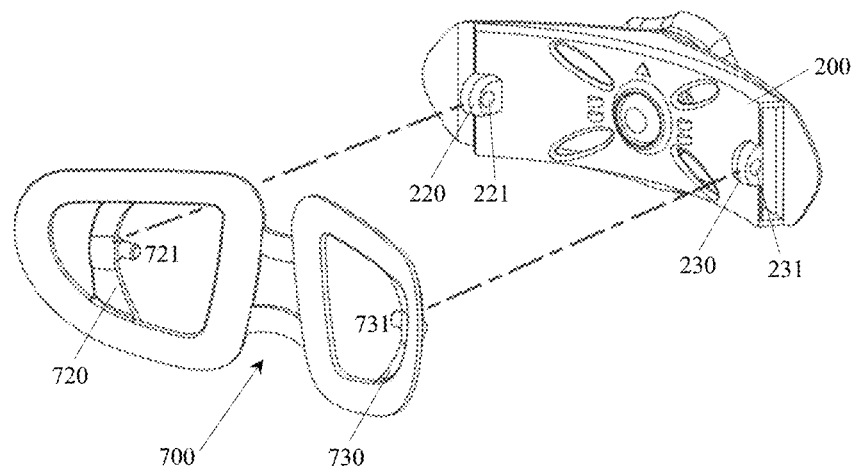
Fig. 5

HEADBAND ARRANGEMENT AND WELDING HELMET EQUIPPED WITH THE SAME

CROSS-REFERENCE TO RELATED APPLICATIONS

This application claims the right of priority of Chinese Patent Application No. 201620864542.8, filed on Aug. 10, 2016, the contents of which are incorporated herein by reference.

FIELD

The present application generally relates to a headband arrangement and a welding helmet, especially an auto-darkening welding helmet, equipped with the headband arrangement.

BACKGROUND OF THE INVENTION

Welding helmets have become essential devices on welding sites for protecting welders. A welding helmet generally comprises a helmet shell and a headband arrangement disposed in the helmet shell. A protection sheet is mounted on the helmet shell to protect a welder's eyes. The headband arrangement is connected to the helmet shell and can be used to be directly worn on the welder's head.

A helmet mounting structure provided at a side of each ear of the welder is used to connect the headband arrangement to the helmet shell. If the welder can adjust the distance between his/her eyes and the protection sheet in case that the welding helmet is worn, it will be more benefit to protect the welder's eyes.

Further, in a conventional headband arrangement, no sufficient flexible cushion structure is provided at a location of protecting the back of the welder's head, such that the same headband arrangement cannot enable wearers whose heads have different shapes (especially the back of the head) to feel comfortable enough, which may indirectly impact the effectiveness of the wearer.

SUMMARY OF THE INVENTION

The present application is mainly aimed at providing an improved headband arrangement for the welding helmet, such that after the headband arrangement is worn on the wearer's head, it is easy for him/her to adjust the position of the headband arrangement relative to the welding helmet, and the worn headband arrangement can be more fitted for the shape of different wears' heads and enable them to feel more comfortable.

In one aspect of the present application, a headband arrangement for a welding helmet is provided, comprising:
  an attachment structure defining several stopping positions therein; and
  a helmet mounting structure which can be selectively slid along the attachment structure, the helmet mounting structure having a lockable component, the lockable component being pivotable about a pivotal shaft between a locking position, in which the lockable component is locked at one of the stopping positions to prevent the helmet mounting structure from sliding, and an unlocking position, in which the lockable component is unlocked to allow the helmet mounting structure to be slidable, wherein a first magnetic part is secured in the lockable component, a second magnetic part is secured in the helmet mounting structure or the attachment structure, and a repulsive force can be generated between the first and second magnetic parts to drive the lockable component to return to the locking position from the unlocking position and to hold the lockable component in the locking position.

In an alternative embodiment, the first magnetic part has a first magnetic side, the second magnetic part has a second magnetic side having the same magnetic polarity as the first magnetic side, and the first and second magnetic parts are disposed in such a way that as the lockable component is pivoted from the locking position to the unlocking position, the first magnetic side faces and approaches the second magnetic side.

In an alternative embodiment, the lockable component has a tongue, the stopping positions are defined by several location holes formed in the attachment structure, the tongue enters one of the location holes in the locking position, and the tongue leaves the location hole in the unlocking position to allow the helmet mounting structure to be slidable.

In an alternative embodiment, the first and/or second magnetic part is a permanent magnet.

In an alternative embodiment, the helmet mounting structure has a bracket in which a socket is defined, and the pivotal shaft and the lockable component are disposed in the socket.

In a preferred embodiment, the second magnetic part is disposed in the socket.

In an alternative embodiment, the attachment structure has a location plate, the location holes are provided in the location plate, and a rail is provided in the location plate to guide the helmet mounting structure.

In a preferred embodiment, the pivotal shaft is substantially parallel to the location plate.

In an alternative embodiment, the second magnetic side of the second magnetic part is substantially parallel to the location plate.

In an alternative embodiment, the lockable component has a handle which is exposed out of an opening of the socket to be accessible.

In an alternative embodiment, an inserting component is received in the socket, the second magnetic part is securely provided in the inserting component, and the inserting component has an edge which defines a scope of moving of the handle in the opening of the socket.

In an alternative embodiment, the headband arrangement comprises a first band part for contacting the forehead of a user and a second band part for contacting the top of the user's head, and the first and second band parts are adjacent to each other and pivotable.

In an alternative embodiment, the attachment structure comprises two attachment structures at two laterally opposite sides of the headband arrangement, the helmet mounting structure also comprises two helmet mounting structures, and each attachment structure is assigned to one helmet mounting structure.

In an alternative embodiment, after the headband arrangement is worn, each attachment structure is above one ear of the user.

In an alternative embodiment, after the helmet mounting structure is mounted on the welding helmet, a space is left between the welding helmet and the handle to be accessible by one's finger.

In an alternative embodiment, the headband arrangement comprises a third band part for attaching at or adjacent to the back of a user's head, the third band part is provided with a sheath for adjusting the third band part's length, and a cushion structure is pivotally provided on a side of the sheath facing the back of the user's head.

In an alternative embodiment, at least two lugs are provided on the side of the sheath facing the back of the user's head, each lug has a substantially horizontal hole, the cushion structure is provided with at least two pivotal pins, and each pin can be inserted into one hole in such a way that the cushion structure is pivotable relative to the sheath.

In an alternative embodiment, a sweat-absorbing pad is provided on a side of the cushion structure facing the back of the user's head.

In an alternative embodiment, the cushion structure can be pivoted with respect to the sheath in an angular range of about 90 degrees.

In another aspect of the present application, a headband arrangement for a welding helmet is provided, which comprises a band part for attaching at or adjacent to the back of a user's head, wherein the band part is provided with a sheath for adjusting the band part's length, and a cushion structure is pivotally provided on a side of the sheath facing the back of the user's head.

In an alternative embodiment, at least two lugs are provided on the side of the sheath facing the back of the user's head, each lug has a substantially horizontal hole, the cushion structure is provided with at least two pivotal pins, and each pin can be inserted into one hole in such a way that the cushion structure is pivotable relative to the sheath.

In an alternative embodiment, a sweat-absorbing pad is provided on a side of the cushion structure facing the back of the user's head.

In an alternative embodiment, the cushion structure can be pivoted with respect to the sheath in an angular range of about 90 degrees.

In another aspect of the present application, a welding helmet, especially an auto-darkness welding helmet, is provided, comprising a headband arrangement as recited in any one of the previously recited headband arrangement.

BRIEF DESCRIPTION OF THE DRAWINGS

As a part of the description and in order to provide further explanation of the present invent, the drawings illustrate preferred embodiments of the present invention, and together with the description are used to explain the principle of the present invention. In the drawings:

FIGS. 4a and 4b schematically illustrate how to adjust the helmet mounting structure relative to the headband arrangement;

FIG. 5 schematically illustrates a cushion structure according to an embodiment of the present application, which is located on a rear sheath of the headband arrangement.

DETAILED DESCRIPTION OF EMBODIMENTS

Figure 1:
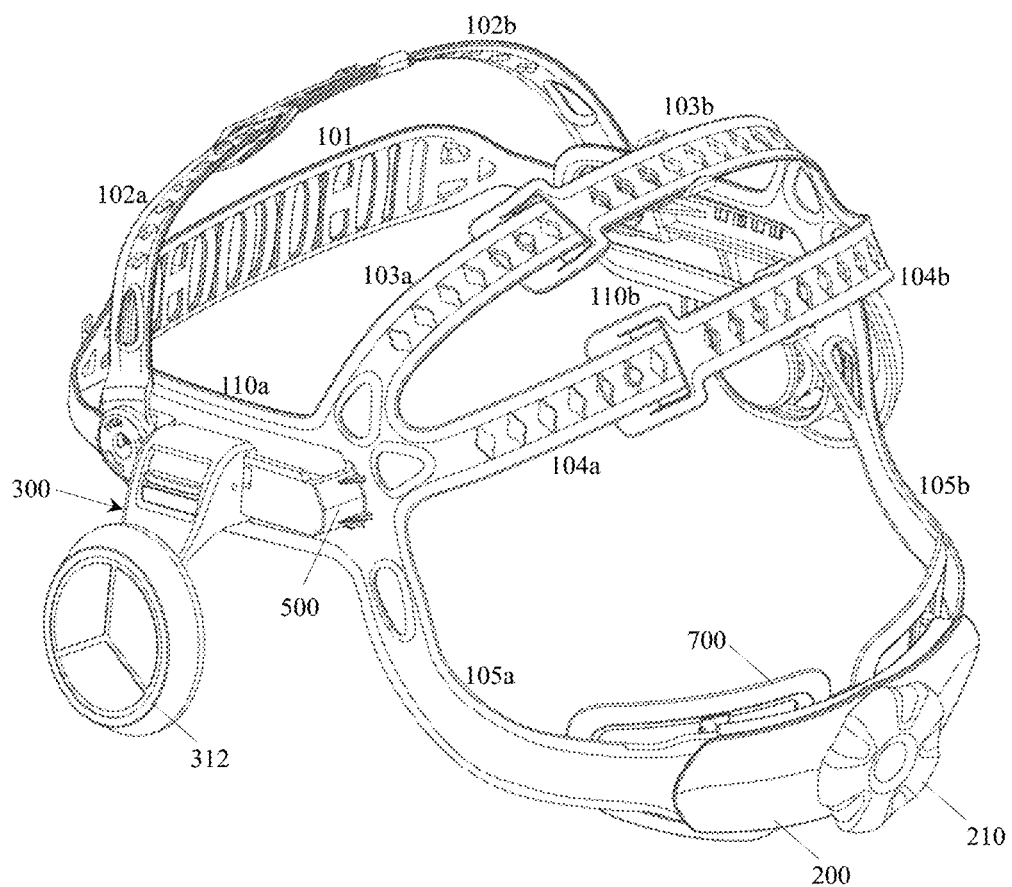
FIG. 1 is a perspective view schematically illustrating a headband arrangement for a welding helmet according to an embodiment of the present application.

In drawings of the present application, the same or similar features are represented by the same reference numerals.

FIG. 1 is a perspective view schematically illustrating a headband arrangement 10 for a welding helmet (not shown) according to an embodiment of the present application. It is noted that in the context of the present application, the cited welding helmet can also be used to refer to an auto-darkening welding helmet. Generally, the welding helmet comprises a helmet shell and the headband arrangement 10 disposed within the helmet shell. In order to protect eyes of a wearer who will do welding work, a protection sheet is mounted on the helmet shell.

The headband arrangement 10 can be made of a plastic material. As shown in FIG. 1, the headband arrangement comprises several band parts 101, 102a, 102b, 103a, 103b, 104a, 104b, 105a, and 105b. The band part 101 is used to bear against the wearer's forehead. The band parts 102a, 102b, 103a, 103b, 104a, and 104b are used to bear against the top of the wearer's head. The band parts 105a and 105b are used to attach at or around the back of the wearer's head.

The headband arrangement 10 also comprises two lateral band parts 110a and 110b. The band parts 103a, 104a, and 105a are provided to integrally extend from the lateral band part 110a. The band parts 103b, 104b, and 105b are provided to integrally extend from the lateral band part 110b. For instance, each of pairs of the band parts 102a and 102b, 103a and 103b, and 104a and 104b are provided with an engaging structure by which the tightness of the headband arrangement 10 to be worn can be adjusted.

Further, each of the band parts 105a and 105b is provided with a toothed slot at one end. The ends of the two band parts can be inserted into a rear sheath 200 made of a plastic material in such a way that the ends are partly overlapped. A rotary knob 210 is rotatably installed on the rear sheath 200. A gear cooperating with the rotary knob 210 is provided in the rear sheath 200. The gear also engages with the toothed slots of the band parts 105a and 105b such that by positively or negatively rotating the knob 210, the two band parts 105a and 105b can be displaced with respect to each other to adjust the tightness of the headband arrangement 10.

The band parts 101, 102a, and 102b are pivotably connected to the lateral band parts 110a and 110b respectively such that when the headband arrangement 10 is worn by the wear, the band parts 101, 102a, and 102b are more fitted for the forehead of wears whose heads have different shapes.

An attachment structure 500 is provided on each of the lateral band parts 110a and 110b of the headband arrangement 10, and is used to cooperate with a helmet mounting structure 300. For instance, the lateral band part can be integrally formed with the attachment structure. The helmet mounting structure 300 is used to be secured in a corresponding fixation hole of the welding helmet so as to secure the headband arrangement 10 to the welding helmet.

Using the helmet mounting structure 300 according to the embodiment, the wearer can readily adjust the position of the welding helmet relative to the headband arrangement 10 forwards or backwards after the welding helmet is worn by him/her. Because the helmet mounting structures 300 at both lateral sides of the headband arrangement 10 are symmetrically provided, only the helmet mounding structure 300 cooperating with the attachment structure 500 on the lateral band part 110a now will be explained with respect to FIGS. 2 to 4b. A skilled person in the art should understand that contents of the explained helmet mounting structure can be applied for the attachment structure 500 on the other lateral band part 110b.

Figure 2:
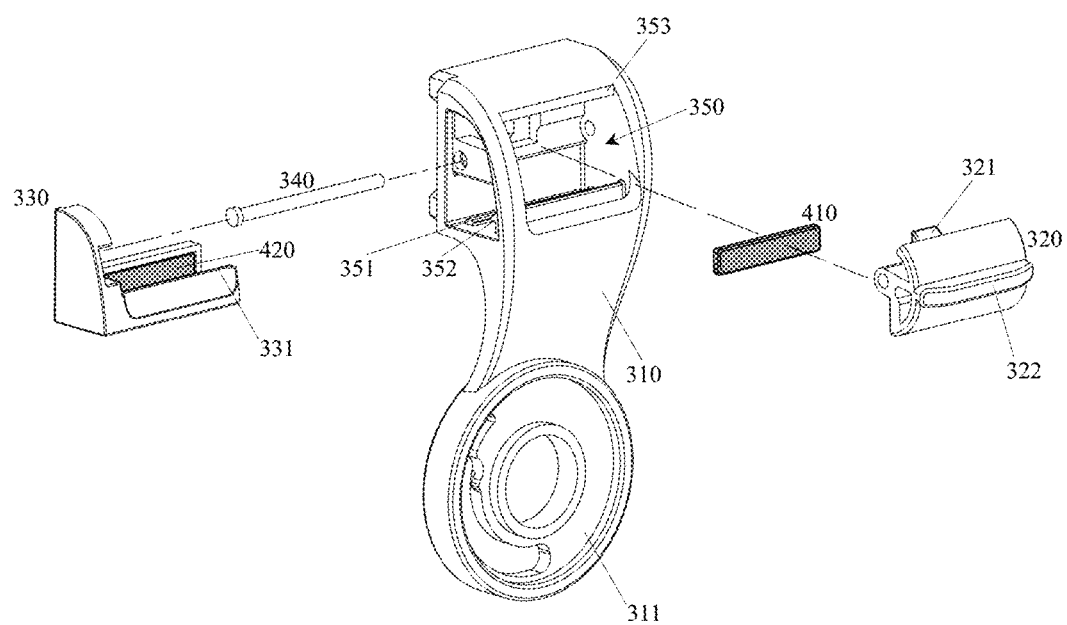
FIG. 2 is an exploded and perspective view schematically illustrating a bracket of a helmet mounting structure of the headband arrangement of FIG. 1.

As shown in FIG. 2, the helmet mounting structure 300 comprises a bracket 310. A knob mating part 311 is provided at one end of the bracket 310 to mate with a knob 312 (see FIG. 1) such that it can be secured in a mounting hole of the welding helmet. The bracket 310 is formed with a socket 350 at an end opposing the knob mating part 311. Housed in the socket 350 are a pivotal shaft 340 and a lockable component 320 which is pivotable about the pivotal shaft 340. For example, an inserting component 330 can be inserted in the socket 350 of the bracket 310.

In the embodiment shown by FIG. 2, the pivotal shaft 340 and the inserting component 330 can be installed into the socket 350 through a lateral opening of the bracket 310 and the lockable component 320 can be installed into the socket 350 through another opening of the bracket 310, such that the pivotal shaft 340 can pass through both a hole of the bracket 310 in the socket 350 and a hole of the lockable component 320 to enable the lockable component 320 to be pivotable about the pivotal shaft 340. A handle 322 is integrally formed in an outer surface of the lockable component 320. When the lockable component 320 is assembled in place, the inserting component 330 causes the area of the opening, through which the lockable component 320 is installed, of the bracket 310 to be narrowed and the handle 322 can be exposed out of the opening of the bracket 310 such that the handle is accessible by one's finger. An edge 331 of the inserting component 330 and an edge 353 of the opening of the bracket 310 limit a range in which the handle 322 is movable. That is to say, the lockable component 320 can be pivoted in the socket 350 about the pivotal shaft 340 only in an angular range prescribed by the edges 331 and 353.

Figure 3A:
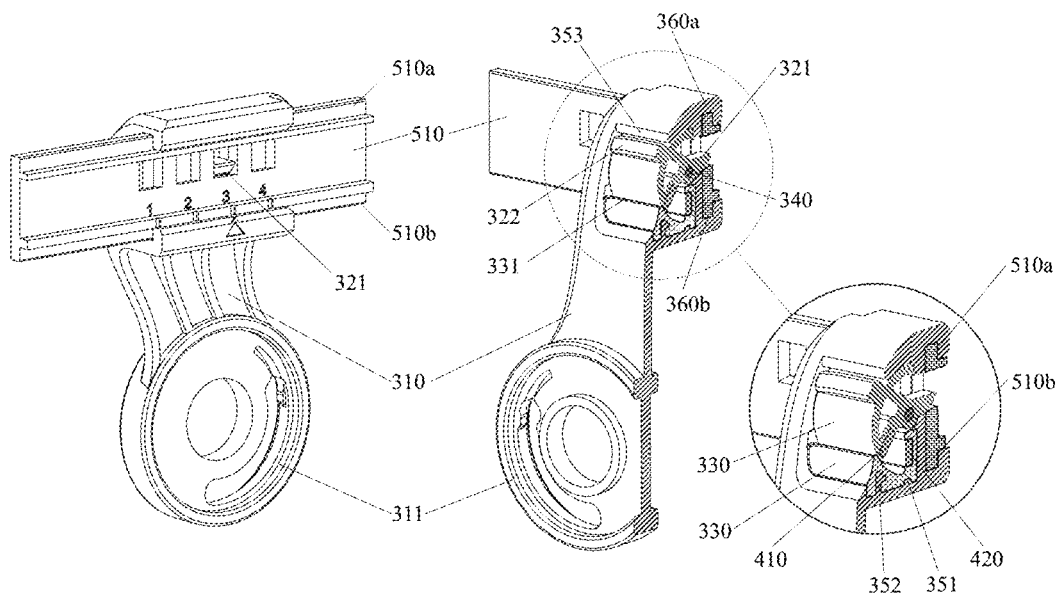
FIGS. 3a and 3b schematically illustrate that the helmet mounting structure is in locked and unlocked states respectively.
Figure 3B:
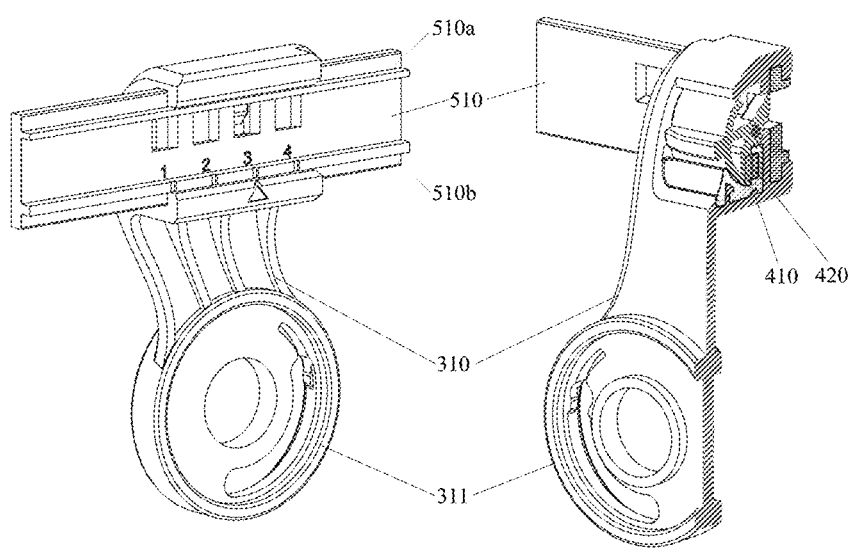

Further as shown in FIGS. 3a and 3b, a guiding rib 351 and a snapping rib 352 are formed in the socket 350. These ribs are used to engage corresponding grooves of the inserting component 330 so as to secure the inserting component 330 in the socket 350. A groove is formed in the inserting component 330 to receive a magnetic part 420, and a groove is formed in the lockable component 320 to receive a magnetic part 410. In the illustrated embodiment, the magnetic part 410, 420 is a flat and cubical body. In an alternative embodiment, the magnetic part can be shaped as a plate. In another alternative embodiment, the magnetic parts 420 and 410 can be adhered to the inserting component 330 and the lockable component 320 by an adhesive respectively. Each magnetic part has N and S magnetic polarities in its opposite surfaces respectively.

Each attachment structure 500 has a location plate 510. Several location holes are formed in the location plate 510 longitudinally. For instance, in FIGS. 3a and 3b, four location holes are formed. A pair of rails 510a and 510b are formed in two opposite longitudinal edges of the location plate 510 respectively. As shown in FIGS. 3a and 3b, a pair of grooves 360a and 360b is formed at a side of the bracket 310 opposite to the socket 350. The grooves 360a and 360b can engage the rails 510a and 510b respectively such that the bracket 310 can be longitudinally guided and moved along the location plate 510. The pivotal shaft 340 can be substantially parallel to the location plate 510. The magnetic part 420 can also be substantially parallel to the location plate 510.

A (lock) tongue 321 is integrally formed in the lockable component 320 at a location substantially opposing the handle 322. An opening is formed in a wall of the bracket 310, which wall forms part of the socket 350 and faces the location plate 510. For instance, when the lockable component 320 is pivoted about the pivotal shaft 340 into a locking position where the component contacts the edge 353, the tongue 321 of the lockable component 320 can pass through the opening of the wall of the bracket 310 and one location hole of the location plate 510 such that the bracket 310 is longitudinally locked with respect to the location plate 510. The magnetic parts 410 and 420 are arranged in the lockable and inserting components 320 and 330 respectively in such a way that circumferentially opposing surfaces or substantially opposing surfaces of the two magnetic parts have the same magnetic polarity. In case that the magnetic part 420 is omitted, the lockable component 320 in the locking position shown in FIG. 3a will pivot downwards about the pivotal shaft 340 due to the component's gravity. However, due to the existence of the magnetic part 420, a repulsive force generated between the magnetic parts 410 and 420 due to the same magnetic polarity repels the gravity to enable the lockable component 320 to be held in the locking position.

In a preferred embodiment, the magnetic part can be a permanent magnet, for example a NdFeB magnet, an AlNiCo magnet, an ferrite magnet or any other suitable magnet. The magnetism of the magnetic parts 410 and 420 should be designed such that the repulsive force generated between them is sufficient to drive the lockable component 320 to pivot about the pivotal shaft 340 into the locking position and to be kept there immovable. Further, the repulsive force should be not so great that it is hard to move the magnetic parts 410 and 420 close to each other.

When the lockable component 320 is pivoted about the pivotal shaft 340 into an unlocking position where the magnetic parts 410 and 420 bear against each other, the tongue 321 can leave the location hole of the location plate 510 and retract into the opening of the wall of the bracket 310 such that the tongue 321 will not hamper longitudinal sliding of the wall of the bracket 310 over the plate 510 under guidance of the rails 510a and 510b. When the lockable component 320 is in the unlocking position, the repulsive force between the magnetic parts 410 and 420 reaches its maximum. Therefore, after the bracket 310 is moved along the location plate 510 to a position relating to another location hole, the lockable component 320 can be pivoted into the locking position by the repulsive force such that the tongue 321 enters said another location hole to lock the bracket 310 to the location plate 510.

FIGS. 4a and 4b schematically illustrate how the helmet mounting structure according the embodiment is adjusted with respect to the headband arrangement. FIG. 4a illustrates that the helmet mounting structure 300 is normally in the locking position. It can be thought that the welding helmet (not shown) has been secured to the helmet mounting structure 300 in place. A space/gap is left between the welding helmet and the headband arrangement 10, which space/gap is large enough so as to allow a finger of the wearer to enter. When it is desirable to move the welding helmet relative to the headband arrangement 10, the finger of the wearer first presses the handle 322 to enable the tongue 321 of the helmet mounting structure 300 to leave the location hole where the tongue is located, such that the helmet mounting structure 300 can be in the unlocking position. Then, as shown in FIG. 4b, after the helmet mounting structure 300 is moved along an arrow A or B to a stopping position relating to another location hole with the helmet mounting structure 300 being held in the unlocking position, the handler 322 is released such that the tongue 321 enters said another location hole such that the helmet mounting structure 300 is locked to the location plate 510 again.

As shown in FIGS. 3a and 3b, four location holes in the location plate 510 define four stopping positions 1, 2, 3, 4 to which the welding helmet can be moved forwards or backwards, such that the wearer can readily adjust the distance between the protection sheet and his/her eyes without taking off the welding helmet.

In the already mentioned embodiments, the helmet mounting structure 300 or the welding helmet is locked by the repulsive force between the two magnetic parts. Such contactless locking can be carried out conveniently. No spring element is needed in the helmet mounting structure 300, and thus its configuration is simplified and its lifetime is prolonged.

The helmet mounting structure is not limited to those embodiments explained previously. For instance, in an alternative embodiment, the inserting component 330 can be omitted, and the magnetic part 420 can be directly provided in the wall of the bracket 310 facing the location plate 510. In another alternative embodiment, the magnetic part 420 even can be directly provided in the location plate 510 as long as the repulsive force between the two magnetic parts 410 and 420 is great enough to drive the lockable component 320 to pivot about the pivotal shaft 340 to the locking position and thus to be kept there immovable. In this embodiment, even the wall of the bracket 310 facing the location plate 510 can be omitted. In another alternative embodiment, the magnetic parts 410 and 420 can be arranged such that they do not contact each other in the unlocking position; however, the repulsive force generated between the magnetic parts in the unlocking position should be greater than that generated in the locking position.

In an alternative embodiment, the location hole and the tongue can be interchanged with each other. For example, one location hole can be provided in part of the lockable component 320, and several tongues can be provided in the location plate 510. In this case, the stopping positions of the location plate 510 will be defined by the tongues. The bracket 310 will be redesigned such that when the lockable component 320 is in the unlocking position, no tongue enters the location hole and the bracket 310 can be slid along the location plate 510; and when the lockable component 320 is in the locking position, one tongue enters the location hole to prevent the bracket 310 from sliding along the location plate 510.

Turning to FIG. 5, a cushion structure 700 according to an embodiment of the present application is illustrated. The cushion structure 700 is installed on the rear sheath 200 such that the cushion structure can be pivoted to a certain extent to contact the back of the wearer's head. Two lugs 220 and 230 are formed on a side of the rear sheath 200 facing the back of the wearer's head. The two lugs 220 and 230 are formed with two substantially horizontal through holes 221 and 231 respectively.

The cushion structure 700 is a single piece made of a plastic material. The cushion structure 700 has a left supporting rib 720 and a right supporting rib 730. The supporting rib 720 has a pivotal pin 721, and the supporting rib 730 has a pivotal pin 731. The pivotal pin 721 has an exposing end and a root end connected to the supporting rib 720. The pivotal pin 731 has an exposing end and a root end connected to the supporting rib 730. Both exposing ends face each other. Each of the lugs 220 and 230 has an inner side facing the other's inner side. Each lug has an outer side opposite to its own inner side.

The supporting ribs 720 and 730 are provided such that the horizontal distance between the root ends of the pivotal pins 721 and 731 is equal to or slightly less than the horizontal distance between the outer sides of the lugs 220 and 230, such that after the root ends of the pivotal pins 721 and 731 are attached on the outer sides of the lugs 220 and 230 respectively and the pivotal pins 721 and 731 pass through the holes 221 and 231 respectively, the pivotal pin 721 in the hole 221 and the pivotal pin 731 in the hole 231 define a pivotal shaft about which the cushion structure 700 can be pivoted. Therefore, the cushion structure 700 is pivotally mounted on the rear sheath 200. It is appreciated by the person skilled in the art that more through-holed lugs and more pivotal pins can be provided in the sheath 200 and cushion structure 700 respectively such that the latter can be more reliably pivoted. In an alternative embodiment, the lug and the pivotal pin can be interchanged with each other. For example, the lug can be provided in the cushion structure 700 and the pivotal pin can be provided in the sheath 200. In an alternative embodiment, the hole can be a blind hole provided on a side of the lug facing the root end of the pivotal pin.

Figure 6:
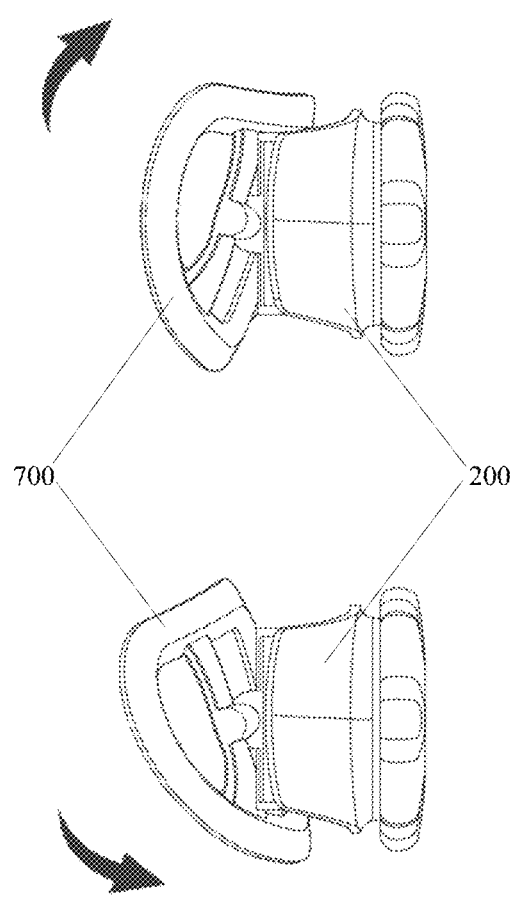
FIG. 6 schematically illustrates the cushion structure of FIG. 5 in two different pivoted states.

As shown in FIG. 6, because the cushion structure 700 can be pivoted upwards or downwards, the headband arrangement can be more fitted for the shape of the back of the wearer's head. The cushion structure 700 and the sheath 200 can be designed in their configuration such that the distance between the cushion structure 700 and the sheath 200 can be changed. In this way, an angle, by which the cushion structure 700 is pivoted relative to the sheath 200, can be adjusted. In a preferred embodiment, the cushion structure 700 can be pivoted relative to the sheath 200 in an angular range of about 90 degrees. For example, the cushion structure 700 can be pivoted upwards or downwards about 45 degrees relative to the horizontal plane. In an alternative embodiment, a sweat-absorbing pad can be provided on a side of the cushion structure 700 intending to contact the back of the wearer's head, to avoid slipping of the headband arrangement caused by sweat of the wearer. In one embodiment of the present application, the cushion structure 700 can be solely provided in a headband arrangement.

Any examples shown in the figures and described above illustrate but do not limit the present application. Other examples are possible. Therefore, the foregoing description should not be construed to limit the scope of the present application, which is defined in the following claims.

Other embodiments are within the following claims and non-limiting examples.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A headband arrangement for a welding helmet, comprising:
   an attachment structure defining several stopping positions therein; and
   a helmet mounting structure configured to selectively slide along the attachment structure and including a lockable component that is pivotable about a pivotal shaft between (i) a locking position, in which the lockable component is locked at one of the stopping positions to prevent the helmet mounting structure from sliding, and (ii) an unlocking position, in which the lockable component is unlocked to allow the helmet mounting structure to be slidable,
   wherein:
      a first magnetic part is secured in the lockable component,
      a second magnetic part is secured in the helmet mounting structure or the attachment structure, and
      a repulsive force is generated between the first magnetic part and the second magnetic part to drive the lockable component to return to the locking position from the unlocking position and to hold the lockable component in the locking position.

2. The headband arrangement as recited in claim 1, wherein:
   the first magnetic part comprises a first magnetic side,
   the second magnetic part comprises a second magnetic side having the same magnetic polarity as the first magnetic side, and
   the first and second magnetic parts are disposed in such a way that as the lockable component is pivoted from the locking position to the unlocking position, the first magnetic side faces and approaches the second magnetic side.

3. The headband arrangement as recited in claim 2, wherein:
   the attachment structure comprises a location plate,
   several location holes are provided in the location plate, and
   a rail is provided in the location plate to guide the helmet mounting structure.

4. The headband arrangement as recited in claim 3, wherein the pivotal shaft is parallel to the location plate.

5. The headband arrangement as recited in claim 3, wherein the second magnetic side of the second magnetic part is parallel to the location plate.

6. The headband arrangement as recited in claim 1, wherein:
   the lockable component comprises a tongue,
   the stopping positions are defined by several location holes formed in the attachment structure,
   the tongue is inserted into one of the several location holes in the locking position, and
   the tongue is removed from the location hole in the unlocking position to allow the helmet mounting structure to be slidable.

7. The headband arrangement as recited in claim 1, wherein at least one of the first magnetic part or second magnetic part is a permanent magnet.

8. The headband arrangement as recited in claim 1, wherein:
   the helmet mounting structure comprises a bracket that includes a socket, and
   the pivotal shaft and the lockable component are disposed in the socket.

9. The headband arrangement as recited in claim 8, wherein the second magnetic part is disposed in the socket.

10. The headband arrangement as recited in claim 8, wherein the lockable component comprises a handle that is exposed out of an opening of the socket to be accessible.

11. The headband arrangement as recited in claim 10, wherein:
   an inserting component is received in the socket,
   the second magnetic part is securely provided in the inserting component, and
   the inserting component comprises an edge that defines a scope of movement of the handle in the opening of the socket.

12. The headband arrangement as recited in claim 1, wherein:
   the attachment structure comprises two attachment structures at two laterally opposite sides of the headband arrangement,
   the helmet mounting structure comprises two helmet mounting structures,
   each of the two attachment structures is assigned to one of the two helmet mounting structures, and
   after the headband arrangement is worn by a user, the attachment structure is located above an ear of the user.

13. The headband arrangement as recited in claim 1, further comprising:
   a third band part configured to attach at or adjacent to a back of a head of a user and provided with a sheath for adjusting a length of the third band part, and
   a cushion structure pivotally provided on a side of the sheath facing the back of the head of the user.

14. The headband arrangement as recited in claim 13, wherein:
   the sheath comprises at least two lugs on the side of the sheath facing the back of the head of the user,
   each of the at least two lugs comprises a horizontal hole,
   the cushion structure comprises at least two pivotal pins, and
   each of the at least two pivotal pins is configured to be inserted into one of the horizontal holes so that the cushion structure is pivotable relative to the sheath.

15. A headband arrangement for a welding helmet, the headband arrangement comprising:

a band part configured to attach at or adjacent to a back of a head of a user and comprising a sheath for adjusting a length of the band part, wherein the sheath comprises a cushion structure pivotally provided on a side of the sheath facing the back of the head of the user and comprising:
- a first supporting rib including a first pivotal pin, the first pivotal pin including a root end connected to the first supporting rib and an exposing end; and
- a second supporting rib including a second pivotal pin, the second pivotal pin including a root end connected to the second supporting rib and an exposing end, wherein the exposing end of the first pivotal pin faces the exposing end of the second pivotal pin.

16. The headband arrangement as recited in claim 15, wherein:
- the sheath comprises a first lug and a second lug on the side of the sheath facing the back of the head of the user,
- each of the first lug and the second lug comprises a horizontal hole, and
- the exposing end of the first pivotal pin is configured to be inserted into the horizontal hole of the first lug and the exposing end of the second pivotal pin is inserted into the horizontal hole of the second lug so that the cushion structure is pivotable relative to the sheath.

17. The headband arrangement as recited in claim 16, wherein:
- the first supporting rib and the second supporting rib are provided such that a horizontal distance between the root end of the first pivotal pin and the root end of the second pivotal pin is equal to or less than a horizontal distance between an outer end of first lug and an outer end of the second lug; and
- the root end of the first pivotal pin is attached on the outer end of the first lug and the root end of the second pivotal pin is attached on the outer end of the second lug.

18. The headband arrangement as recited in claim 16, wherein where the exposing end of the first pivotal pin is inserted into the horizontal hole of the first lug and the exposing end of the second pivotal pin is inserted into the horizontal hole of the second lug defines a pivotal shaft about which the cushion structure is configured to pivot relative to the sheath in an angular range of about 90 degrees.

19. The headband arrangement as recited in claim 15, wherein the cushion structure is configured to pivot relative to the sheath in an angular range of about 90 degrees.

20. An auto-darkening welding helmet, comprising a headband arrangement, wherein the headband arrangement comprises:
- an attachment structure defining several stopping positions therein; and
- a helmet mounting structure configured to selectively slide along the attachment structure and including a lockable component that is pivotable about a pivotal shaft between (i) a locking position, in which the lockable component is locked at one of the stopping positions to prevent the helmet mounting structure from sliding, and (ii) an unlocking position, in which the lockable component is unlocked to allow the helmet mounting structure to be slidable, wherein:
- a first magnetic part is secured in the lockable component,
- a second magnetic part is secured in the helmet mounting structure or the attachment structure, and
- a repulsive force is generated between the first magnetic part and the second magnetic part to drive the lockable component to return to the locking position from the unlocking position and to hold the lockable component in the locking position.

* * * * *